United States Patent
Xu et al.

(10) Patent No.: US 9,968,922 B2
(45) Date of Patent: May 15, 2018

(54) CATALYST FOR PRODUCING PARAXYLENE BY CO-CONVERSION OF METHANOL AND/OR DIMETHYL ETHER AND C4 LIQUEFIED GAS, METHOD FOR PREPARING THE SAME AND METHOD FOR USING THE SAME

(75) Inventors: Lei Xu, Liaoning (CN); Zhongmin Liu, Liaoning (CN); Zhengxi Yu, Liaoning (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 185 days.

(21) Appl. No.: 14/366,209

(22) PCT Filed: Apr. 26, 2012

(86) PCT No.: PCT/CN2012/074709
§ 371 (c)(1),
(2), (4) Date: Jun. 17, 2014

(87) PCT Pub. No.: WO2013/091337
PCT Pub. Date: Jun. 27, 2013

(65) Prior Publication Data
US 2014/0343337 A1  Nov. 20, 2014

(30) Foreign Application Priority Data

Dec. 19, 2011 (CN) .......................... 2011 1 0428610

(51) Int. Cl.
| | | |
|---|---|---|
| *B01J 31/26* | (2006.01) | |
| *B01J 29/40* | (2006.01) | |
| *C07C 2/86* | (2006.01) | |
| *B01J 31/02* | (2006.01) | |

(52) U.S. Cl.
CPC .............. *B01J 31/26* (2013.01); *B01J 29/40* (2013.01); *B01J 29/405* (2013.01); *B01J 31/0204* (2013.01); *B01J 31/0274* (2013.01); *B01J 31/0275* (2013.01); *C07C 2/862* (2013.01); *C07C 2/864* (2013.01); *C07C 2/865* (2013.01); *B01J 2229/186* (2013.01); *B01J 2229/32* (2013.01); *B01J 2231/005* (2013.01); *C07C 2521/04* (2013.01); *C07C 2521/08* (2013.01); *C07C 2521/16* (2013.01); *C07C 2523/06* (2013.01); *C07C 2523/08* (2013.01); *C07C 2529/40* (2013.01); *Y02P 20/52* (2015.11); *Y02P 30/20* (2015.11)

(58) Field of Classification Search
CPC .. C07C 2/00; C07C 2/76; C07C 15/00; C07C 15/08
USPC .................................................. 585/411, 415
See application file for complete search history.

(56) References Cited

U.S. PATENT DOCUMENTS

| | | | | |
|---|---|---|---|---|
| 5,019,663 | A | * | 5/1991 | Chou ........................ C07C 2/00 585/415 |
| 2010/0041932 | A1 | * | 2/2010 | Dodwell .................. B01J 29/06 585/469 |
| 2010/0261941 | A1 | * | 10/2010 | Hagemeister ........... C07C 2/864 585/470 |
| 2014/0275468 | A1 | * | 9/2014 | Kellett .................... C07C 37/50 528/308.3 |

FOREIGN PATENT DOCUMENTS

CN          101607858 A   * 12/2009

OTHER PUBLICATIONS

Translation of CN101607858A.*
Translated Description of CN101607858A.*
Translated PCT Written Opinion for WO2013091337 (The Instant Invention).*
Halgeri et al. ("Recent advances in selectivation of zeolites for para-disubstituted aromatics." Catalysis Today 73.1 (2002): 65-73).*
Cannella ("Xylenes and Ethylbenzene." Kirk-Othmer Encyclopedia of Chemical Technology, Pub. Oct. 19, 2007).*

* cited by examiner

*Primary Examiner* — Brian A McCaig
*Assistant Examiner* — Jason Y Chong
(74) *Attorney, Agent, or Firm* — Albert Bordas, P.A.

(57) ABSTRACT

This application provides a catalyst for producing paraxylene by co-conversion of methanol and/or dimethyl ether and $C_4$ liquefied gas, and preparation and application thereof. The catalyst is an aromatization molecular sieve catalyst with a shape-selective function co-modified by bimetal and siloxane compound. Methanol and/or dimethyl ether and $C_4$ liquefied gas are fed in reactor together, wherein aromatization reaction occurring on a modified shape-selective molecular sieve catalyst. The yield of aromatics is effectively improved, in which paraxylene is the main product. In products obtained by co-conversion of methanol and/or dimethyl ether and $C_4$ liquefied gas, the yield of aromatics is greater than 70 wt %, and the content of paraxylene in aromatics is greater than 80 wt %, and the selectivity of paraxylene in xylene is greater than 99 wt %.

3 Claims, No Drawings

CATALYST FOR PRODUCING PARAXYLENE BY CO-CONVERSION OF METHANOL AND/OR DIMETHYL ETHER AND C4 LIQUEFIED GAS, METHOD FOR PREPARING THE SAME AND METHOD FOR USING THE SAME

TECHNICAL FIELD

The present disclosure relates to a method for producing paraxylene by co-conversion of methanol and/or dimethyl ether and $C_4$ liquefied gas. More specifically, the present disclosure relates to a highly selective catalyst for producing paraxylene by co-conversion of methanol and/or dimethyl ether and $C_4$ liquefied gas. Further, the present disclosure relates to a preparation method and the application of said catalyst.

BACKGROUND

Paraxylene is a basic raw material for producing polyester. Presently, paraxylene is mainly obtained by disproportionation, isomerization, adsorption separation or cryogenic separation of a raw material containing toluene, $C_9$ aromatics and mixed xylene from naphtha catalytic reforming products. By this method, the target product paraxylene ratio in mixed $C_8$ aromatics is only about 20% due to the reason that the reaction of producing paraxylene is controlled by thermodynamics. Its equipment is huge with high operating costs due to the large recycle material quantity, and an expensive adsorption separation system is necessary because a high purity paraxylene product cannot be obtained by common distillation.

With the increasing shortage of oil resource, many research institutes in domestic and overseas began to work actively on development of new techniques for producing aromatics, such as producing aromatics from methanol, or from liquefied gas etc. Methanol to aromatics technology provided a new pathway to prepare aromatics from coal or natural gas, wherein aromatics can be directly obtained by aromatization reaction of methanol or dimethyl ether on a composite catalyst containing metal and zeolite.

In 1977, Mobil's Chang et al (*Journal of Catalysis*, 1977, 47, 249) reported a method to prepare aromatics and other hydrocarbons on ZSM-5 zeolite catalysts from methanol or other oxygenates. It showed that alkanes and olefins can be converted to aromatics under certain conditions under the effect of metal components. Therefore, it has become a main research direction that the ZSM-5 zeolite catalysts are modified by metal component to produce more aromatics by conversion of methanol.

At present, the modification of ZSM-5 zeolite catalysts are mainly focused on using Zn and Ga, while the use of other metals such as Ag, Cu have also been reported. Ono et al (J Chem. Soc, Faraday Trans. 1, 1988, 84 (4), 1091; Microporous Materials, 1995, 4, 379) investigated the catalytic performance of methanol to aromatics (MTA) process on the ZSM-5 zeolite catalysts which were modified by Zn and Ag using ion exchange method. It revealed that the yield of aromatics in products increased to about 67.4% (C %) after ZSM-5 zeolite was modified by Zn, and increased to about 80% after ZSM-5 zeolite was modified by Ag.

CN 101244969 discloses a fluidized bed apparatus, containing an aromatization reactor of $C_1$-$C_2$ hydrocarbon or methanol and a catalyst regeneration system. By adjusting catalyst coking state in aromatization reactor, a continuous efficient conversion of $C_1$-$C_2$ hydrocarbons or methanol to aromatics with high selectivity is realized.

CN 1880288 discloses a process with high total aromatics selectivity, and which can be operated flexibly. As the main product, aromatics are obtained from methanol conversion on modified ZSM-5 zeolite catalysts.

A ZSM-5 zeolite catalyst loaded by Zn and Mn is disclosed in U.S. Pat. No. 4,615,995. The catalyst is used for methanol conversion to olefin and aromatics. In products, the ratio of low carbon olefins to aromatics can be controlled by adjusting the content of Zn and Mn loaded in catalyst.

It is an effective way to expand the sources of aromatics by the aromatization of liquefied petroleum gas (LPG) from oil refinery byproducts. In process of LPG aromatization to aromatics, the high quality gasoline and aromatics such as benzene, toluene and xylene (BTX) can be obtained simultaneously. U.S. Pat. No. 4,642,402 discloses a process of light hydrocarbons conversion to aromatics, which is developed by UOP, converting $C_3$ and $C_4$ to BTX aromatics by aromatization reaction on a ZSM-5 zeolite catalyst modified by Ga, wherein the aromatics yield is about 60%.

A HZSM-5 zeolite catalyst modified by gallium, zinc, platinum is disclosed in CN 1023633C, using for aromatization reaction of low carbon alkane. The catalyst is applicable for aromatization of $C_5$-$C_8$ alkane, especially olefins to the mixed aromatics containing benzene, toluene and xylene. The total aromatics yield is about 50 wt %.

CN 1660724A discloses a fluidized bed process which is used for aromatization of liquefied gas to benzene, toluene and xylene on DLC-2 catalyst, and the total yield of benzene, toluene and xylene is about 65 wt %.

The said conversion processes of methanol or liquefied gas to aromatics, which all utilize one single raw material to obtain the target mix aromatics: benzne, toluene and xylene (BTX), possess low market value, and thus poor economic profit.

DISCLOSURE

The present application provides a catalyst for producing high-yield aromatics by co-conversion of methanol and/or dimethyl ether and $C_4$ liquefied gas; a method for preparing the said catalyst and the application of the said catalyst. And more specifically, the present application provides a high-yield process for producing aromatics using the said catalyst. By combining methanol from coal and $C_4$ liquefied gas from oil refinery byproducts as the raw material, the said process can obtain aromatics as much as possible. Meanwhile, the yield of aromatics can be effectively improved by combining methanol aromatization and liquefied gas aromatization.

The present application further provides a process for producing high-yield paraxylene by co-conversion of methanol and/or dimethyl ether and $C_4$ liquefied gas. Methanol and/or dimethyl ether and $C_4$ liquefied gas co-convert to paraxylene by aromatization reaction and shape-selective alkylation reaction on the molecular sieve catalyst with a shape-selective function co-modified by bimetal and siloxane compound.

The present application provides a catalyst for producing paraxylene, by co-conversion of methanol and/or dimethyl ether and $C_4$ liquefied gas. Said catalyst is an aromatization molecular sieve catalyst with a shape-selective function co-modified by bimetal and siloxane compound, wherein said bimetal are Zinc and Gallium, wherein said siloxane compound has structural formula as Formula I,

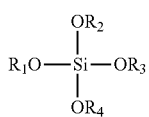

(Formula I)

wherein, $R_1$, $R_2$, $R_3$ and $R_4$ are independently selected from $C_1$-$C_{10}$ alkyl group.

In a preferable embodiment, said siloxane compound is tetraethoxysilane.

In a preferable embodiment, the method of modifying molecular sieve in combination by bimetal and siloxane compound comprise the steps as follows: (a) the molecular sieve is impregnated in a solution containing at least one soluble salt of one of Zinc and Gallium, then filtered, dried and calcined to obtain a metal-modified molecular sieve; (b) said metal-modified molecular sieve obtained from step (a) is impregnated in a solution containing at least one soluble salt of the other of Zinc and Gallium, then filtered, dried and calcined to obtain a bimetal-modified molecular sieve; (c) said bimetal-modified molecular sieve obtained from step (b) is impregnated in a siloxane compound, then filtered, dried and calcined to obtain said aromatization molecular sieve catalyst co-modified by bimetal and siloxane compound.

In a preferable embodiment, the molecular sieve used in said aromatization molecular sieve catalyst with a shape-selective function is HZSM-5 and/or HZSM-11 zeolite molecular sieve.

In a preferable embodiment, the loading amount of said Zinc is 0.5-8 wt % of the total weight of said catalyst; and the loading amount of said Gallium is 0.5-8 wt % of the total weight of said catalyst; and the loading amount of said siloxane compound, which is based on silicon oxide, is 0.5-10 wt % of the total weight of said catalyst.

In other aspect, the present application provides a method for preparing any one of said catalysts, comprising the steps as follows:
  (a) a zeolite molecular sieve is impregnated in a solution containing at least one soluble salt of one of Zinc and Gallium, then filtered, dried and calcined to obtain a metal-modified molecular sieve;
  (b) said metal-modified molecular sieve obtained from step (a) is impregnated in a solution containing at least one soluble salt of the other of Zinc and Gallium, then filtered, dried and calcined to obtain a bimetal-modified molecular sieve;
  (c) said bimetal-modified molecular sieve obtained from step (b) is impregnated in a siloxane compound, then filtered, dried and calcined to obtain said aromatization molecular sieve catalyst co-modified by bimetal and siloxane compound.

In other aspect, the present application provides a process for producing paraxylene by co-conversion of methanol and/or dimethyl ether and $C_4$ liquefied gas, comprising the steps of: a gas mixture containing methanol and/or dimethyl ether and $C_4$ liquefied gas is passed through a reactor producing paraxylene by aromatization reaction; wherein any one of said catalyst according to claim 1-4 is loaded into said reactor; wherein said aromatization reaction is carried out at a temperature of 350-550° C., a pressure between atmospheric pressure to 5 MPa and a weight hourly space velocity of said gas mixture between 0.1 $h^{-1}$ to 20 $h^{-1}$.

In the present application, the yield of aromatics is more than 70 wt % in the non-aqueous products from the aromatization of methanol and/or dimethyl ether and $C_4$ liquefied gas; and the selectivity of paraxylene in aromatics is more than 80 wt %; and the selectivity of paraxylene in xylene isomers is more than 99 wt %.

In a preferable embodiment, said process is conducted in a fixed bed or a fluidized bed reactor.

DETAILED EMBODIMENTS

Specifically, the present application provides a catalyst for producing paraxylene, by co-conversion of methanol and/or dimethyl ether and $C_4$ liquefied gas. Said catalyst is an aromatization molecular sieve catalyst with a shape-selective function co-modified by bimetal and siloxane compound, wherein said bimetal are Zinc and Gallium.

In the present application, said aromatization molecular sieve catalyst co-modified by bimetal and siloxane compound is obtained by the steps as follows:
  (a) the raw powder of zeolite molecular sieve containing a template agent is ion-exchanged with $NH_4^+$, then calcined to obtain an acidic zeolite molecular sieve;
  (b) said acidic zeolite molecular sieve obtained from step (a) is impregnated in a solution containing one soluble salt, then filtered, dried and calcined to obtain a metal-modified molecular sieve;
  (c) said metal-modified molecular sieve obtained from step (b) is impregnated in solution containing the other soluble salt, then filtered, dried and calcined to obtain a bimetal-modified molecular sieve;
  (d) said bimetal-modified molecular sieve obtained from step (c) is modified by impregnating in a siloxane compound, adjusting the external surface acidity and pore structure to obtain said catalyst co-modified by bimetal and siloxane compound; and
  (e) said catalyst co-modified by bimetal and siloxane compound obtained from step (d) is molded by compression or spray drying technology.

Said bimetal are Zinc and Gallium.

In the present application, modification method using siloxane compound is also known as silanization modification.

Step (1) can be skipped when the zeolite molecular sieve is H-zeolite molecular sieve. And the silanization modification can be carried out before the bimetal-modification.

Wherein, said siloxane compound has structural formula as Formula I,

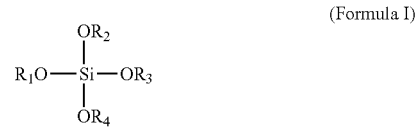

(Formula I)

wherein, $R_1$, $R_2$, $R_3$ and $R_4$ are independently selected from $C_1$-$C_{10}$ alkyl group.

Wherein, said $C_1$-$C_{10}$ alkyl group contain methyl, ethyl, n-propyl, isopropyl, n-butyl, isobutyl, tertiary butyl, pentyl, hexyl, heptyl, nonyl and decyl. Said alkyl group contain all isomers, when there are isomers. For example, propyl group contain n-propyl and isopropyl, and butyl contain n-butyl, isobutyl and tertiary butyl.

In a preferable embodiment, said siloxane compound is liquid at room temperature. When said siloxane compound is solid at room temperature, it should be heated into liquid before used for impregnation.

In said catalyst modified by bimetal and siloxane compound, the loading amount of each metal is 0.5-8 wt % of the total weight of said catalyst; and the loading amount of said siloxane compound, which is based on silicon oxide, is 0.5-10 wt % of the total weight of said catalyst.

In a preferable embodiment, the molecular sieve used in said catalyst is HZSM-5 and/or HZSM-11 zeolite molecular sieve. In a further preferable embodiment, the molecular sieve used in said catalyst is HZSM-5 zeolite molecular sieve. In a preferable embodiment, said siloxane compound is tetraethoxysilane (all of $R_1$, $R_2$, $R_3$ and $R_4$ is ethyl).

In the present application, the mixture of methanol and/or dimethyl ether and $C_4$ liquefied gas is used as a raw material, wherein said methanol is pure methanol or an aqueous solution of methanol, and the mass percentage concentration of methanol in aqueous solution is 50-100%. Said raw material can be mixed by methanol and/or dimethyl ether and $C_4$ liquefied gas in any proportion. Although methanol, dimethyl ether or $C_4$ liquefied gas can be used independently as a raw material, a higher yield of aromatics is obtained when the raw material is the mixture of methanol and/or dimethyl ether and $C_4$ liquefied gas. In a preferable embodiment, the weight ratio of methanol and/or dimethyl ether to $C_4$ liquefied gas in the raw material is (10-90):(90-10). In a further preferable embodiment, the weight ratio of methanol and/or dimethyl ether to $C_4$ liquefied gas in the raw material is (30-70):(70-30).

In present application, the process for producing paraxylene by co-conversion of methanol and/or dimethyl ether and $C_4$ liquefied gas is conducted in a fixed bed or a fluidized bed reactor. The reaction is carried out at a temperature of 350-550° C., preferably at a temperature of 400-500° C. The reaction is carried out at a pressure between atmospheric pressure to 5 MPa, preferably at a pressure between atmospheric pressure to 2 MPa. The reaction is carried out at a weight hourly space velocity of said gas mixture between 0.1 $h^{-1}$ to 20 $h^{-1}$, preferably at a weight hourly space velocity of said gas mixture between 1 $h^{-1}$ to 10 $h^{-1}$.

DETAILED DESCRIPTION OF EMBODIMENT

The present application is described in details by referring to the following Examples, but not limited to the Examples.

In the following Examples, the reagents and raw materials are all obtained by commercial purchase and wt % means the weight percentage, unless indicated otherwise. In present application, the parts, percentages and amounts are all based on weight, unless indicated otherwise.

Example 1: Preparation of a Catalyst Used in Fixed Bed 1) 500 g of the raw powder containing a template agent inside of ZSM-5 zeolite molecular sieve (from The Catalyst Plant of Nankai University, molar ratio of $SiO_2/Al_2O_3$=50) was calcined at 550° C. to remove the template agent, and then ion-exchanged four times with 0.5 mol/L ammonium nitrate solution at water-bath 80° C., and then dried out in air at 120° C., and then calcined at 550° C. for 3 hours. Then HZSM-5 zeolite molecular sieve was obtained.

2) 20 g of the HZSM-5 zeolite molecular sieve obtained from step 1) was impregnated in zinc nitrate [$Zn(NO_3)_2$] solution with mass percent concentration of 5% at room temperature for 4 hours, and then dried out at 120° C. after the supernatant liquid was decanted, and then calcined in air 550° C. for 6 hours to obtain a zinc metal-modified HZSM-5 zeolite molecular sieve.

3) The zinc metal-modified HZSM-5 zeolite molecular sieve obtained from step 2) was impregnated in gallium nitrate [$Ga(NO_3)_2$] solution with mass percent concentration of 8% at room temperature for 4 hours, and then dried out at 120° C. after the supernatant liquid was decanted, and then calcined in air 550° C. for 6 hours to obtain a gallium and zinc bimetal-modified HZSM-5 zeolite molecular sieve.

4) The gallium and zinc bimetal-modified HZSM-5 zeolite molecular sieve obtained from step 3) was impregnated in tetraethoxysilane (TEOS) at room temperature for 24 hours, and then dried out at 120° C. after the supernatant liquid was decanted, and then calcined in air 550° C. for 6 hours to obtain a HZSM-5 zeolite molecular sieve catalyst co-modified by gallium and zinc bimetal and siloxane compound, which was named as CPX-01.

Example 2: Preparation of a Catalyst Used in Fixed Bed 1) 20 g of the HZSM-5 zeolite molecular sieve obtained from step 1) in Example 1 was impregnated in gallium nitrate [$Ga(NO_3)_2$] solution with mass percent concentration of 10% at room temperature for 4 hours, and then dried out at 120° C. after the supernatant liquid was decanted, and then calcined in air 550° C. for 6 hours to obtain a gallium metal-modified HZSM-5 zeolite molecular sieve.

2) The gallium metal-modified HZSM-5 zeolite molecular sieve obtained from step 1) was impregnated in a zinc nitrate [$Zn(NO_3)_2$] solution with mass percent concentration of 8% at room temperature for 4 hours, and then dried out at 120° C. after the supernatant liquid was decanted, and then calcined in air 550° C. for 6 hours to obtain a gallium and zinc bimetal-modified HZSM-5 zeolite molecular sieve.

3) The gallium and zinc bimetal-modified HZSM-5 zeolite molecular sieve obtained from step 2) was impregnated in tetraethoxysilane (TEOS) at room temperature for 24 hours, and then dried out at 120° C. after the supernatant liquid was decanted, and then calcined in air 550° C. for 6 hours to obtain a HZSM-5 zeolite molecular sieve catalyst co-modified by gallium and zinc bimetal and siloxane compound, which was named as CPX-02.

Example 3: Preparation of a Catalyst Used in Fluidized Bed 1) 200 g of the HZSM-5 zeolite molecular sieve obtained from step 1) in Example 1 was impregnated in zinc nitrate [$Zn(NO_3)_2$] solution with mass percent concentration of 10% at room temperature for 4 hours, and then dried out at 120° C. after the supernatant liquid was decanted, and then calcined in air 550° C. for 6 hours to obtain a zinc metal-modified HZSM-5 zeolite molecular sieve.

2) The zinc metal-modified HZSM-5 zeolite molecular sieve obtained from step 1) was impregnated in a gallium nitrate [$Ga(NO_3)_2$] solution with mass percent concentration of 15% at room temperature for 4 hours, and then dried out at 120° C. after the supernatant liquid was decanted, and then calcined in air 550° C. for 6 hours to obtain a gallium and zinc bimetal-modified HZSM-5 zeolite molecular sieve.

3) The gallium and zinc bimetal-modified HZSM-5 zeolite molecular sieve obtained from step 2) was impregnated in tetraethoxysilane (TEOS) at room temperature for 24 hours, and then dried out at 120° C. after the supernatant liquid was decanted, and then calcined in air 550° C. for 6 hours to obtain a HZSM-5 zeolite molecular sieve co-modified by gallium and zinc bimetal and siloxane compound.

4) The HZSM-5 zeolite molecular sieve co-modified by gallium and zinc bimetal and siloxane compound from step 3) was mixed with kaoline, silica sol, alumina sol and deionized water into slurry. The mass ratio of the zeolite molecular sieve:kaoline:dry basis of silica sol:dry basis of alumina sol was 30:32:26:12. And the solid content in the slurry was about 35 wt %. And then the slurry was aged at room temperature for 5 hours, and then molded by spray drying after grinded by colloid mill to obtain the microsphere catalyst with the particle size of 20-100 μm. Elemental analysis showed that based on the total weight of the catalyst, the catalyst contained 2.3 wt % zinc, 3.1 wt % gallium, and 5.3 wt % siloxane compound calculated according to silicon oxide. The catalyst was named as CPX-03.

Example 4: Catalyst Evaluation in Fixed Bed Reactor

CPX-01 from Example 1 and CPX-02 from Example 2 were used as the catalysts in the reaction. 5 g catalyst was loaded in a fixed bed reactor, and then treated in air at 550° C. for 1 hour followed by a cooling process in nitrogen to reach the reaction temperature of 450° C., 0.15 MPa. Methanol and $C_4$ liquefied gas were pumped into a vaporizer, mixed into raw materials at a temperature of 200° C., and then contacted with the catalyst in the reactor. The raw materials with methanol and $C_4$ liquefied gas in ratio of 50:50 were fed in the reactor with a total weight hourly space velocity of 2 $h^{-1}$. Distribution of raw materials and waterless products were shown in Table 1. On CPX-01 catalyst and CPX-02 catalyst, the yields of aromatics in waterless products were 71.31 wt % and 73.03 wt %, and the contents of paraxylene in aromatics were 87.17 wt % and 86.67 wt %, and the selectivities of paraxylene in xylene isomers were 99.41 wt % and 99.32 wt %, respectively.

TABLE 1

Distribution of raw materials and waterless products

| Catalyst | CPX-01 | CPX-02 |
|---|---|---|
| Yield of aromatics in hydrocarbons (wt %) | 71.31 | 73.03 |
| Content of paraxylene in aromatics (wt %) | 87.17 | 86.67 |
| Selectivity of paraxylene in xylene isomers (wt %) | 99.41 | 99.32 |

| | Distribution of raw materials and products (wt %) | | |
|---|---|---|---|
| | raw materials | products | products |
| methanol | 50.00 | | |
| $C_3$ | 0.81 | | |
| $C_4$ alkane | 10.96 | | |
| $C_4$ olefins | 37.52 | | |
| $C_5^+$ | 0.72 | | |
| $C_1$-$C_5$ | | 28.69 | 26.97 |
| benzene | | 0.02 | 0.02 |
| methylbenzene | | 0.45 | 0.45 |
| ethylbenzene | | 0.62 | 0.63 |
| paraxylene | | 62.16 | 63.29 |
| m-xylene | | 0.06 | 0.08 |
| o-xylene | | 0.31 | 0.36 |
| $C_9^+$ | | 7.69 | 8.20 |
| Total | 100.00 | 100.00 | 100.00 |

*$C_5^+$: hydrocarbons with carbon number not less than five; $C_9^+$: hydrocarbons with carbon number not less than nine.

Example 5: Catalyst Evaluation in Fixed Bed

CPX-01 from Example 1 and CPX-02 from Example 2 were used as the catalysts in the reaction. 5 g catalyst was loaded in a fixed bed reactor, and then treated in air at 550° C. for 1 hour followed by a cooling process in nitrogen to reach the reaction temperature of 450° C., 0.1 MPa. Methanol and $C_4$ liquefied gas were pumped into a vaporizer, mixed into raw materials at a temperature of 200° C., and then contacted with the catalyst in the reactor. The raw materials with methanol and $C_4$ liquefied gas in ratio of 30:70 were fed in the reactor with a total weight hourly space velocity of 2 $h^{-1}$. Distribution of raw materials and waterless products were shown in Table 2. On CPX-01 catalyst and CPX-02 catalyst, the yields of aromatics in waterless products were 75.21 wt % and 79.01 wt %, and the contents of paraxylene in aromatics were 85.88 wt % and 85.74 wt %, and the selectivities of paraxylene in xylene isomers were 99.21 wt % and 99.19 wt %, respectively.

TABLE 2

Distribution of raw materials and products

| Catalyst | CPX-01 | CPX-02 |
|---|---|---|
| Yield of aromatics in hydrocarbons (wt %) | 75.21 | 79.01 |
| Content of paraxylene in aromatics (wt %) | 85.88 | 85.74 |
| Selectivity of paraxylene in xylene isomers (wt %) | 99.21 | 99.19 |

| | Distribution of raw materials and products (wt %) | | |
|---|---|---|---|
| | Raw materials | Products | Products |
| methanol | 30.00 | | |
| $C_3$ | 1.13 | | |
| $C_4$ alkane | 15.34 | | |
| $C_4$ olefins | 52.52 | | |
| $C_5^+$ | 1.01 | | |
| $C_1$-$C_5$ | | 24.79 | 20.99 |
| benzene | | 0.02 | 0.02 |
| methylbenzene | | 0.45 | 0.47 |
| ethylbenzene | | 0.63 | 0.66 |
| paraxylene | | 64.59 | 67.74 |
| m-xylene | | 0.10 | 0.12 |
| o-xylene | | 0.41 | 0.43 |
| $C_9^+$ | | 9.00 | 9.56 |
| Total | 100.00 | 100.00 | 100.00 |

*$C_5^+$: hydrocarbons with carbon number not less than five; $C_9^+$: hydrocarbons with carbon number not less than nine.

Example 6: Catalyst Evaluation in Fluidized Bed

CPX-03 from Example 3 was used as the catalyst in the reaction. 10 g catalyst was loaded in a fluidized bed reactor, and then treated in air at 550° C. for 1 hour followed by a cooling process in nitrogen to reach the reaction temperature of 450° C., 0.1 MPa. Methanol and $C_4$ liquefied gas were pumped into a vaporizer, mixed into raw materials at a temperature of 200° C., and then contacted with the catalyst in the reactor. Two raw materials with methanol and $C_4$ liquefied gas in ratios of 50:50 and 30:70 were fed in the reactor with a total weight hourly space velocity of 2 $h^{-1}$, respectively. Distribution of raw materials and waterless products were shown in Table 2. The yields of aromatics in waterless products were 70.12 wt % and 72.87 wt %, and the contents of paraxylene in aromatics were 84.47 wt % and 85.21 wt %, and the selectivities of paraxylene in xylene isomers were 99.04 wt % and 99.08 wt %, respectively.

TABLE 3

| Distribution of raw materials and products | | |
|---|---|---|
| Catalyst | CPX-03 | CPX-03 |
| Yield of aromatics in hydrocarbons (wt %) | 70.12 | 72.87 |
| Content of paraxylene in aromatics (wt %) | 84.47 | 85.21 |
| Selectivity of paraxylene in xylene isomers (wt %) | 99.04 | 99.08 |

| | Distribution of raw materials and products (wt %) | | | |
|---|---|---|---|---|
| | Raw materials | Products | Raw material | Products |
| methanol | 50.00 | | 30.00 | |
| $C_3$ | 0.81 | | 1.13 | |
| $C_4$ alkane | 10.96 | | 15.34 | |
| $C_4$ olefins | 37.52 | | 52.52 | |
| $C_5^+$ | 0.72 | | 1.01 | |
| $C_1$-$C_5$ | | 29.88 | | 27.13 |
| benzene | | 0.02 | | 0.02 |
| methylbenzene | | 0.44 | | 0.46 |
| ethylbenzene | | 0.61 | | 0.64 |
| paraxylene | | 59.23 | | 62.10 |
| m-xylene | | 0.15 | | 0.16 |
| o-xylene | | 0.42 | | 0.42 |
| $C_9^+$ | | 9.24 | | 9.08 |
| Total | 100.00 | 100.00 | | 100.00 |

*$C_5^+$: hydrocarbons with carbon number not less than five; $C_9^+$: hydrocarbons with carbon number not less than nine.

The invention claimed is:

1. A process for producing paraxylene by co-conversion of methanol and/or dimethyl ether and $C_4$ liquefied gas, comprising the steps as follows:

passing a gas mixture containing methanol and/or dimethyl ether and $C_4$ liquefied gas through a reactor comprising an aromatization molecular sieve catalyst with a shape-selective function to produce paraxylene by aromatization reaction;

wherein said aromatization reaction is carried out at a temperature from 400° C. to 550° C., a pressure from atmospheric pressure to 2 MPa and a weight hourly space velocity of said gas mixture from 1 h$^{-1}$ to 10 h$^{-1}$;

wherein said aromatization molecular sieve catalyst comprises HZSM-5 and/or HZSM-11 zeolite molecular sieve co-modified by bimetal and a siloxane compound;

wherein said bimetal are zinc and gallium;

wherein said siloxane compound has the structural formula

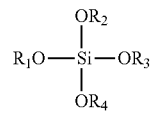

wherein, $R_1$, $R_2$, $R_3$ and $R_4$ are independently selected from $C_1$-$C_{10}$ alkyl group, and wherein a loading amount of said zinc is 0.5-8 wt % of a total weight of said catalyst, a loading amount of said gallium is 0.5-8 wt % of the total weight of said catalyst, and a loading amount of said siloxane compound, which is based on silicon oxide, is 0.5-10 wt % of the total weight of said catalyst;

wherein the process comprises the following step to prepare said aromatization molecular sieve catalyst:

(a) impregnating a molecular sieve comprising HZSM-5 and/or HZSM-11 in a solution containing at least one soluble salt of one of zinc or gallium, which is then filtered, dried and calcined to obtain a metal-modified molecular sieve;

(b) impregnating said metal-modified molecular sieve obtained from step (a) in a solution containing at least one soluble salt of the other of zinc or gallium, which is then filtered, dried and calcined to obtain a bimetal-modified molecular sieve; and (c) impregnating said bimetal-modified molecular sieve obtained from step (b) in a siloxane compound, which is then filtered, dried and calcined to obtain said aromatization molecular sieve catalyst.

2. The process according to claim 1, wherein said siloxane compound is tetraethoxysilane.

3. The process according to claim 1, wherein said process is conducted in a fixed bed or a fluidized bed reactor.